(12) United States Patent
Nobe et al.

(10) Patent No.: US 9,392,980 B2
(45) Date of Patent: Jul. 19, 2016

(54) NUCLEAR MEDICAL IMAGING APPARATUS, IMAGE PROCESSING APPARATUS, AND IMAGE PROCESSING METHOD

(75) Inventors: Masashi Nobe, Utsunomiya (JP); Masatoshi Seki, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 997 days.

(21) Appl. No.: 12/777,509

(22) Filed: May 11, 2010

(65) Prior Publication Data

US 2010/0289813 A1 Nov. 18, 2010

(30) Foreign Application Priority Data

May 13, 2009 (JP) .................................. 2009-116864
Mar. 18, 2010 (JP) .................................. 2010-063222

(51) Int. Cl.
 A61B 6/03 (2006.01)
 G09G 5/02 (2006.01)
 A61B 6/00 (2006.01)

(52) U.S. Cl.
 CPC ................. *A61B 6/032* (2013.01); *A61B 6/037* (2013.01); *A61B 6/5235* (2013.01); *A61B 6/5247* (2013.01)

(58) Field of Classification Search
 CPC ................................. A61B 5/055; A61B 6/037
 See application file for complete search history.

(56) References Cited

U.S. PATENT DOCUMENTS 2,336,380 A * 12/1943 Wilmanns ..................... 430/396
6,205,350 B1 * 3/2001 Lorenz et al. ................. 600/425

(Continued)

FOREIGN PATENT DOCUMENTS

JP   S63-242236   10/1988
JP   08-077329    3/1996

(Continued)

OTHER PUBLICATIONS

C.J.S. Price, et al., Cerebral Neutrophil Recruitment, Histology, and Outcome in Acute Ischemic Stroke: An Imaging-Based Study, Stroke, American Heart Association, 2004, vol. 35, Issue 7, pp. 1659-1664.*

(Continued)

*Primary Examiner* — Robert Sorey
*Assistant Examiner* — Kristine Rapillo
(74) *Attorney, Agent, or Firm* — Oblon, McClelland, Maier & Neustadt, L.L.P.

(57) ABSTRACT

A two-dimensional look-up-table (LUT) storage unit stores a two-dimensional LUT in which each combination of two input values is associated with an output value for outputting a different color tone. A registration unit registers Positron Emission Tomography (PET) images of examination 1 and examination 2 by using X-ray CT images of the examination 1 and the examination 2; and an output-image creating unit acquires from the two-dimensional LUT an output value where input values are a combination of pixel values of corresponding pixels between the registered PET images, and creates an output image. Moreover, the output-image creating unit creates the output image from output values within a setting range specified on the two-dimensional LUT, among acquired output values. A display control unit controls display such that an output image or a composite image of an output image and an X-ray CT image created by a composite-image creating unit is to be displayed on a monitor.

16 Claims, 8 Drawing Sheets

(56) References Cited

U.S. PATENT DOCUMENTS

| | | | |
|---|---|---|---|
| 7,718,971 B2* | 5/2010 | Tanaka | 250/363.07 |
| 7,999,235 B2* | 8/2011 | Kohara et al. | 250/363.1 |
| 8,160,329 B2* | 4/2012 | Inoue | 382/128 |
| 8,174,728 B2* | 5/2012 | Ichitani | 358/1.9 |
| 2006/0058624 A1* | 3/2006 | Kimura | 600/407 |
| 2006/0215889 A1* | 9/2006 | Omi | A61B 6/032 382/128 |
| 2007/0096028 A1 | 5/2007 | Tanaka | |
| 2009/0109497 A1* | 4/2009 | Hattori | H04N 1/387 358/452 |
| 2009/0185756 A1* | 7/2009 | Toyoda et al. | 382/264 |
| 2009/0285460 A1* | 11/2009 | Ishikawa et al. | 382/128 |
| 2013/0129176 A1* | 5/2013 | Hu et al. | 382/131 |

FOREIGN PATENT DOCUMENTS

| | | |
|---|---|---|
| JP | 2001-212138 | 8/2001 |
| JP | 2006-095279 | 4/2006 |
| JP | 2006-211221 | 8/2006 |
| JP | 2007-107995 | 4/2007 |
| WO | WO 2004/089218 | 10/2004 |

OTHER PUBLICATIONS

C.J.S. Price, et al., Cerebral Neutrophil Recruitment, Histology, and Outcome in Acute Ishemic Stroke: An Imaging-Based Study. Stroke. Jul. 2004. vol. 35, Issue 7, pp. 1659-1664.*

Office Action mailed Feb. 25, 2014, in Japanese Patent Application No. 2010-063222 (with English-language Translation).

Kazumi Matsud et al., Local Examination of Epilepsy Focus using SISCOM, Medical Review Co., Ltd., 2008, vol. 2 No. 1, pp. 4-6.

Office Action issued Mar. 3, 2015, in Japanese Patent Application No. 2010-063222.

* cited by examiner

REGISTRATION IN ACCORDANCE WITH MOTION VECTOR

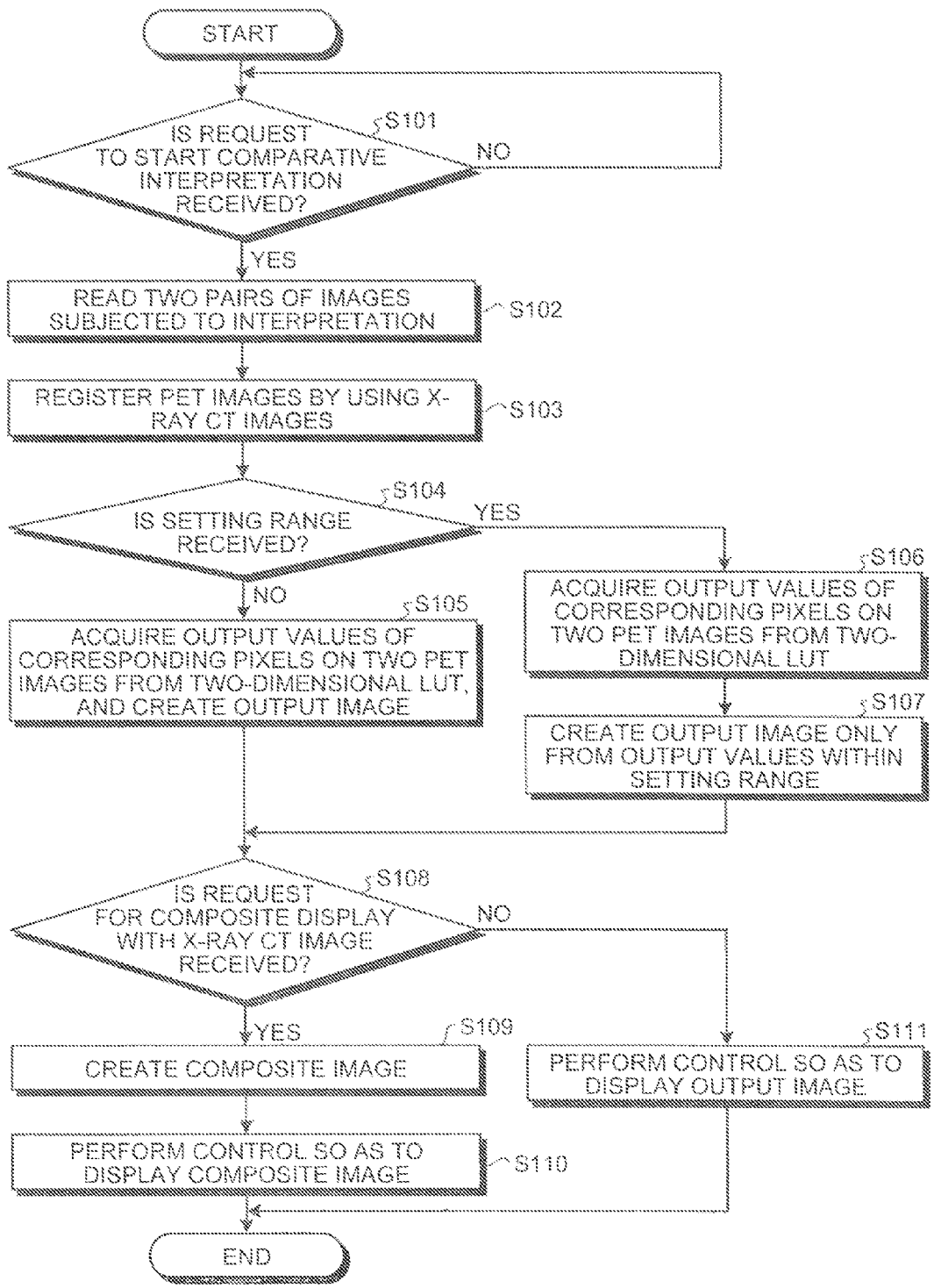

NUCLEAR MEDICAL IMAGING APPARATUS, IMAGE PROCESSING APPARATUS, AND IMAGE PROCESSING METHOD

CROSS-REFERENCE TO RELATED APPLICATIONS

This application is based upon and claims the benefit of priority from the prior Japanese Patent Application No. 2009-116864, filed on May 13, 2009, and Japanese Patent Application No. 2010-063222, filed on Mar. 18, 2010; the entire contents of both of which are incorporated herein by reference.

BACKGROUND

1. Field

Embodiments described herein related generally to a nuclear medical imaging apparatus, an image processing apparatus, and an image processing method.

2. Description of the Related Art

Conventionally, nuclear medical imaging apparatuses, such as a gamma camera, a Single Photon Emission (SPE) Computed Tomography (CT) apparatus (SPECT apparatus), and a Positron Emission CT apparatus (PET apparatus), are widely used in today's medical fields as a medical diagnostic imaging apparatus that can perform a functional diagnosis on living tissue of a subject.

A nuclear medical imaging apparatus measures from the outside of body a gamma ray emitted from an isotope or a labeled compound that is selectively captured into living tissue, and reconstructs a nuclear medical image that a radiation dose distribution of the measured gamma ray is imaged. For example, the nuclear medical imaging apparatus reconstructs a nuclear medical image on which a distribution of tumor tissue that captures an isotope or a labeled compound is rendered, thereby providing functional information about living tissue of a subject to a doctor who performs image diagnosis.

Recently, an apparatus into which a nuclear medical imaging apparatus and an X-ray Computed Tomography (CT) apparatus that images morphological information in living tissue of a subject are integrated (for example, a PET-CT apparatus or a SPECT-CT apparatus) is implemented in practice.

For example, a PET-CT apparatus can acquire a PET image reconstructed by a PET apparatus, and an X-ray CT image reconstructed by an X-ray CT apparatus with respect to the same cross section of a subject, and can simultaneously refer to functional information acquired from the PET image and morphological information acquired from X-ray CT image, thereby enabling a doctor to perform image diagnosis with high precision. Moreover, the PET-CT apparatus can create and display a composite image that a PET image and an X-ray CT image are combined.

Examinations by using a PET-CT apparatus or a SPECT-CT apparatus are generally performed on the same portion of the same subject a plurality of number of times (for example, before treatment and after treatment), and results of the examinations are presented by displaying in parallel layout nuclear medical images that are registered in accordance with X-ray CT images.

However, even if results of examinations before and after a treatment are displayed in parallel layout, it is difficult for a doctor to determine intuitively a detailed difference that is changed owing to the treatment, such as the size of a tumor. Therefore, a technology has been known that a differential image is created by differentiating pixel values (Standard Uptake Value (SUV)) of corresponding pixels on nuclear medical images that are registered in accordance with X-ray CT images, and the created differential image is displayed as a result of a plurality of examinations. In other words, by referring to a differential image, a doctor can objectively determine, for example, a distributional change in tumor tissue that is changed between before and after a treatment.

However, information displayed on the above differential image is only differential information between nuclear medical images of respective examinations subjected to comparison; consequently, the doctor cannot grasp information about original values of respective nuclear medical images subjected to comparison, even by referring to the differential image. As well as differential information, for a doctor who performs image diagnosis, it is important to grasp from what value to what value an SUV value changes in order to determine a region to be focused on for planning courses for a treatment, for example, a region in which a treatment effect is large, a region in which a treatment effect is small, and a region into which a tumor metastasizes.

Although a differential image can be displayed in parallel layout together with a plurality of nuclear medical images subjected to comparison, a doctor performs image diagnosis by referring to three images, so that it is difficult to determine objectively a region to be focused on.

As described above, there is a problem that the above conventional technology does not necessarily assist image diagnosis by a doctor who compares a plurality of examination results.

BRIEF DESCRIPTION OF THE DRAWINGS

FIG. 9 is a flowchart for explaining examination-result display processing by the PET-CT apparatus according to the embodiment.

DETAILED DESCRIPTION

Figure 1:
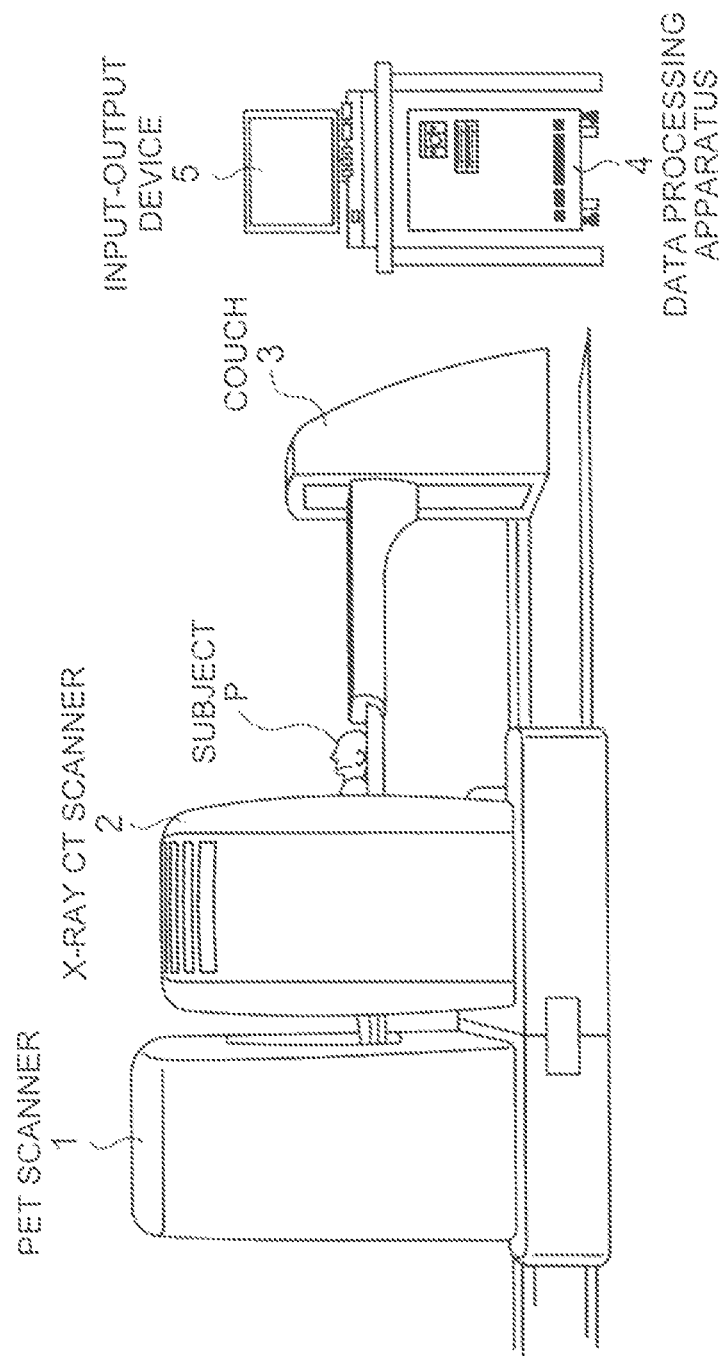
FIG. 1 is a schematic diagram for explaining a configuration of a Positron Emission Tomography (PET)-Computed Tomography (CT) apparatus according to an embodiment.

In one embodiment, a nuclear medical imaging apparatus includes an image creating unit, an association-information storage unit, a registration unit, an output-image creating unit and a display control unit. The image creating unit creates a nuclear medical image by detecting at a certain portion a radiation ray emitted by a nuclide given to a subject. The association-information storage unit stores two-dimensional association information in which each of combinations of two input values is associated with an output value for outputting a different color tone. The registration unit executes registration of a first image and a second image that are nuclear medical images created by the image creating unit in two different time periods, based on tissue images with respect to the certain portion that are acquired at respective moments of creation of the first image and the second image. The output-image creating unit acquires an output value where input values are two pixel values of corresponding pixels between the first image and the second image that are registered by the registration unit, from the two-dimensional association information stored by the association-information storage unit, and creates an output image of which pixel values are acquired output values. The display control unit controls display such that the output image created by the output-image creating unit is to be displayed on a certain display unit.

In another embodiment, an image processing apparatus includes an image creating unit, an association-information storage unit, a registration unit, an output-image creating unit and a display control unit. The image creating unit creates a nuclear medical image by detecting at a certain portion a radiation ray emitted by a nuclide given to a subject. The association-information storage unit stores two-dimensional association information in which each of combinations of two input values is associated with an output value for outputting a different color tone. The registration unit executes registration of a first image and a second image that are nuclear medical images created by the image creating unit in two different time periods, based on tissue images with respect to the certain portion that are acquired at respective moments of creation of the first image and the second image. The output-image creating unit acquires an output value where input values are two pixel values of corresponding pixels between the first image and the second image that are registered by the registration unit, from the two-dimensional association information stored by the association-information storage unit, and creates an output image of which pixel values are acquired output values. The display control unit controls display such that the output image created by the output-image creating unit is to be displayed on a certain display unit.

In still another embodiment, an image processing method includes storing by an association-information storage unit two-dimensional association information in which each of combinations of two input values is associated with an output value for outputting a different color tone. And the image processing method includes executing by a registration unit registration between a first image and a second image that are nuclear medical images created in two different time periods, based on tissue images with respect to a certain portion that are acquired at respective moments of creation of the first image and the second image. And the image processing method includes acquiring by an output-image creating unit an output value where input values are two pixel values of corresponding pixels between the first image and the second image that are registered by the registration unit, from the two-dimensional association information stored by the association-information storage unit, and creating an output image of which pixel values are acquired output values. And the image processing method includes controlling display by a display control unit such that the output image created by the output-image creating unit is to be displayed on a certain display unit.

In still another embodiment, an image processing method includes storing by an association-information storage unit two-dimensional association information in which each of combinations of two input values is associated with an output value for outputting a different color tone. And the image processing method includes executing by a registration unit registration between a first image and a second image that are nuclear medical images created in two different time periods. And the image processing method includes acquiring by an output-image creating unit an output value where input values are respective two pixel values of corresponding pixels between the first image and the second image that are registered by the registration unit, from the two-dimensional association information stored by the association-information storage unit, and creating an output image of which pixel values are acquired output values. And the image processing method includes controlling display by a display control unit such that the output image created by the output-image creating unit is to be displayed on a certain display unit.

Exemplary embodiments of a nuclear medical imaging apparatus, an image processing apparatus, and an image processing method will be explained below in detail with reference to the accompanying drawings. The following description explains a Positron Emission Tomography (PET)-Computed Tomography (CT) apparatus into which a PET apparatus, which is a nuclear medical imaging apparatus, and an X-ray CT apparatus are integrated as an embodiment.

First of all, a configuration of a PET-CT apparatus according to an embodiment is explained below. FIG. 1 is a schematic diagram for explaining a configuration of the PET-CT apparatus according to the embodiment. As shown in FIG. 1, the PET-CT apparatus according to the embodiment includes a PET scanner 1, an X-ray CT scanner 2, a couch 3, a data processing apparatus 4, and an input-output device 5.

The PET scanner 1 includes a gamma-ray detector that is formed in a ring shape and detects a gamma ray, and detects a pair of gamma rays successively emitted from a labeled compound taken up into tissue of a subject P (for example, 18F labeled deoxyglucose that is labeled with "18F (fluorine)", which is a positron emitting nuclide), with the gamma-ray detector during a certain monitoring period. The PET scanner 1 then creates and collects projection data that is based on count values of the detected gamma rays by associating it with gamma-ray detected positions and gamma-ray incident directions by the gamma-ray detector.

The X-ray CT scanner 2 includes an X-ray generating device that generates an X-ray, and an X-ray detector that detects an X-ray; radiates an X-ray from the X-ray generating device onto the subject P; and detects the X-ray that has passed through the subject P with the X-ray detector. Specifically, the X-ray CT scanner 2 rotates the X-ray generating device and the X-ray detector that are arranged on opposite sides of the subject P, about the body axis of the subject P; radiates X-rays onto the subject from multiple directions; and detects the strengths of the X-rays in the respective directions that are attenuated by being absorbed to the body when passing through the inside of the body. The X-ray CT scanner 2 then creates and collects projection data of the detected X-rays by associating it with X-ray detected positions by the X-ray detector.

The couch 3 is a bed on which the subject P is to be placed.

The data processing apparatus 4 creates a PET image and a CT image that are reconstructed by performing back-projection processing on respective projection data collected by the PET scanner 1 and the X-ray CT scanner 2, respectively. The data processing apparatus 4 will be described later.

The input-output device 5 includes input devices, such as a button, a mouse, and a keyboard that receive, for example, various instructions from an operator of the PET-CT apparatus, and receive a request to start comparative interpretation from a doctor who performs comparative interpretation on results of a plurality of examinations performed by the PET-CT apparatus. Moreover, the input-output device 5 includes, for example, a monitor that displays a Graphical User Interface (GUI) for receiving various instructions from an operator and a doctor, and displays an image created b the data processing apparatus 4, and the like.

Specifically, as the PET scanner 1 and the X-ray CT scanner 2 move from left to right in FIG. 1, the PET-CT apparatus according to the embodiment collects projection data of X-ray at first, then collects projection data based on the count value of gamma-ray, and then creates an X-ray CT image and a PET image with respect to the same portion of the subject P with the data processing apparatus 4. More specifically, the PET-CT apparatus according to the embodiment creates an X-ray CT image and a PET image of the same portion of the subject P with respect to each examination, each time when an examination is performed on the subject P at a different time point. For example, the PET-CT apparatus according to the embodiment creates two PET images with respect to the same portion of the subject P through respective examinations that are performed on the subject P before and after a treatment, such as administration of an anticancer agent. In the following description, among examinations performed twice on the same portion of the same subject, an examination that is performed at first (for example, an examination before treatment) is sometimes described as an examination 1, and an examination that is performed after the examination 1 (for example, an examination after treatment) is sometimes described as an examination 2.

The PET-CT apparatus according to the embodiment has a main feature such that the PET-CT apparatus can ensure assistance in image diagnosis by a doctor who compares a plurality of examination results by using nuclear medical images (PET images), through image processing by the data processing apparatus 4, which is explained below in detail.

Figure 2:
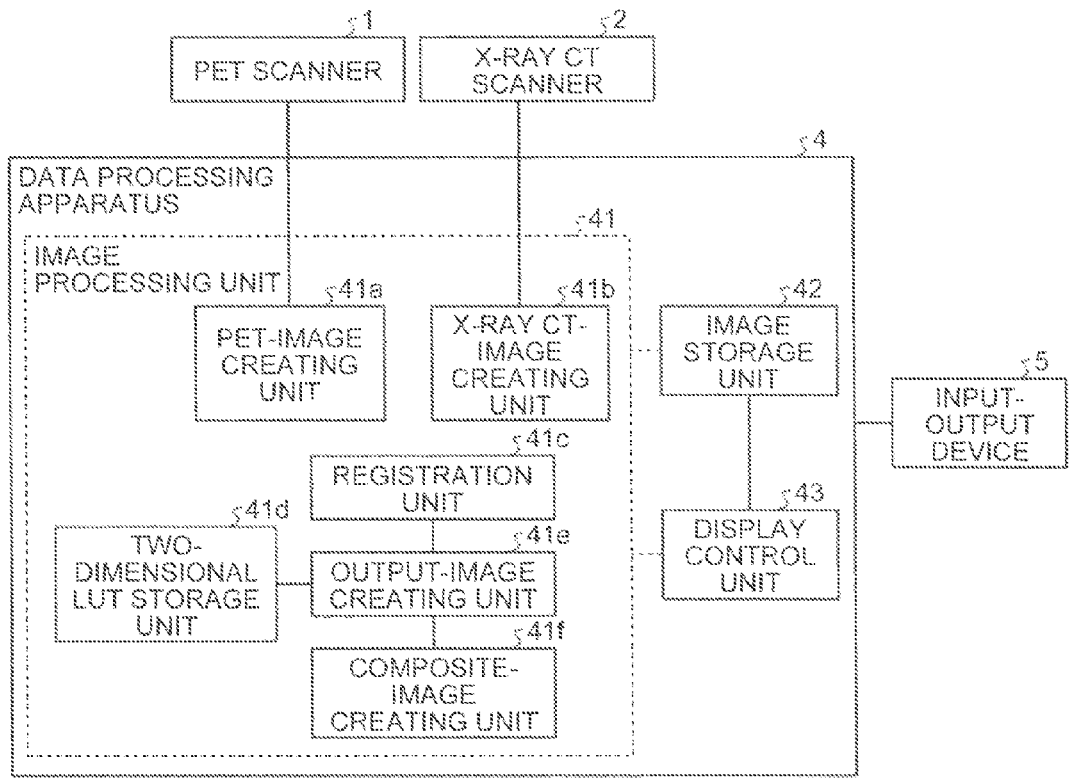
FIG. 2 is a functional block diagram for explaining a configuration of a data processing apparatus.
Figure 3A:
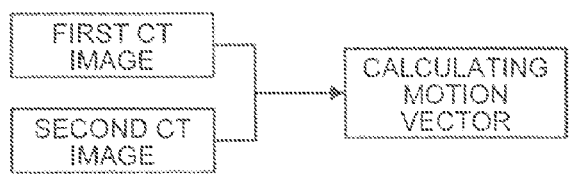
FIGS. 3A and 3B are schematic diagrams for explaining a registration unit.
Figure 3B:
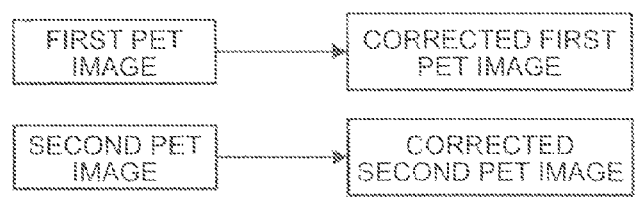
Figure 4:
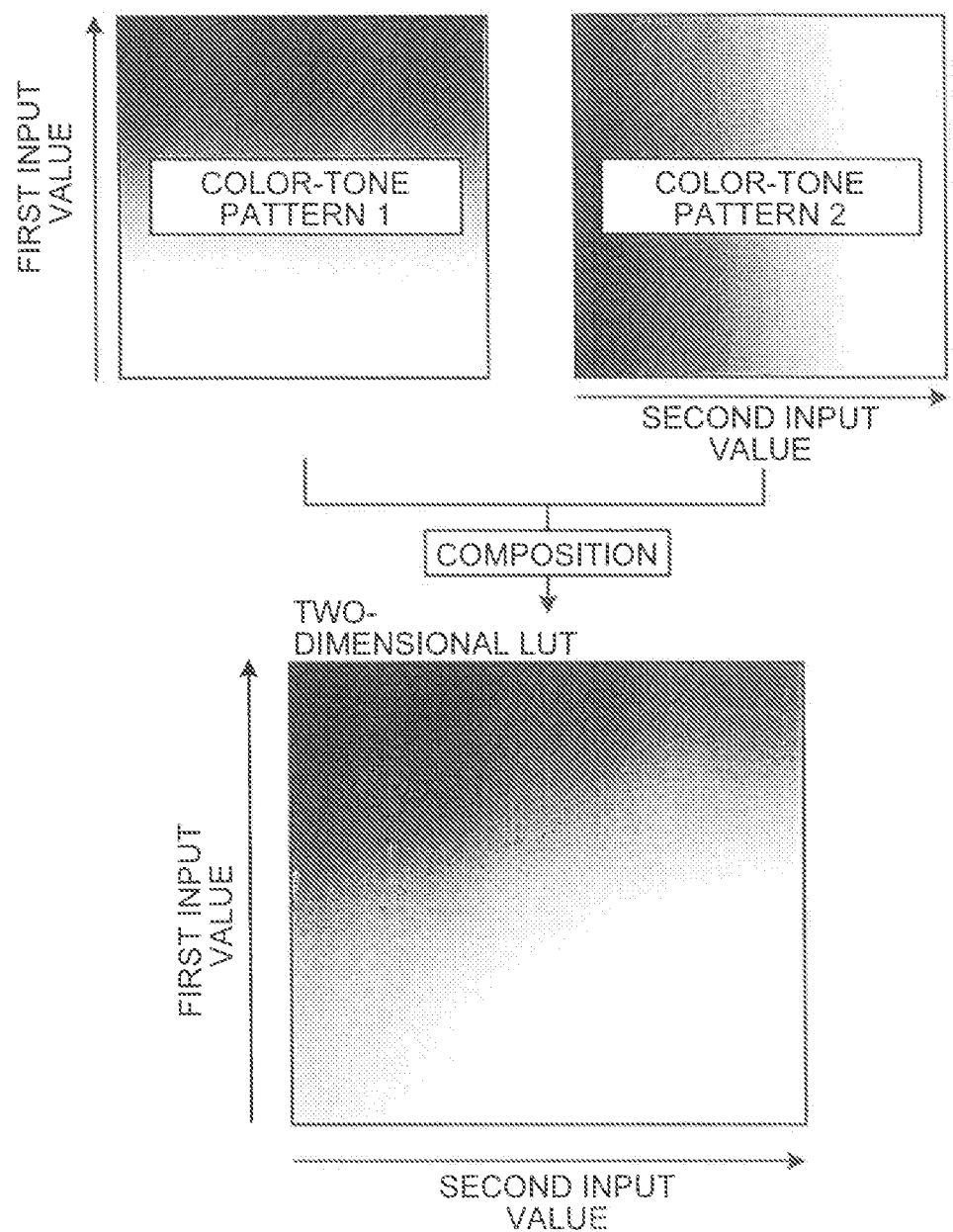
FIG. 4 is a schematic diagram for explaining a two-dimensional look-up-table (LUT) storage unit.
Figure 5A:
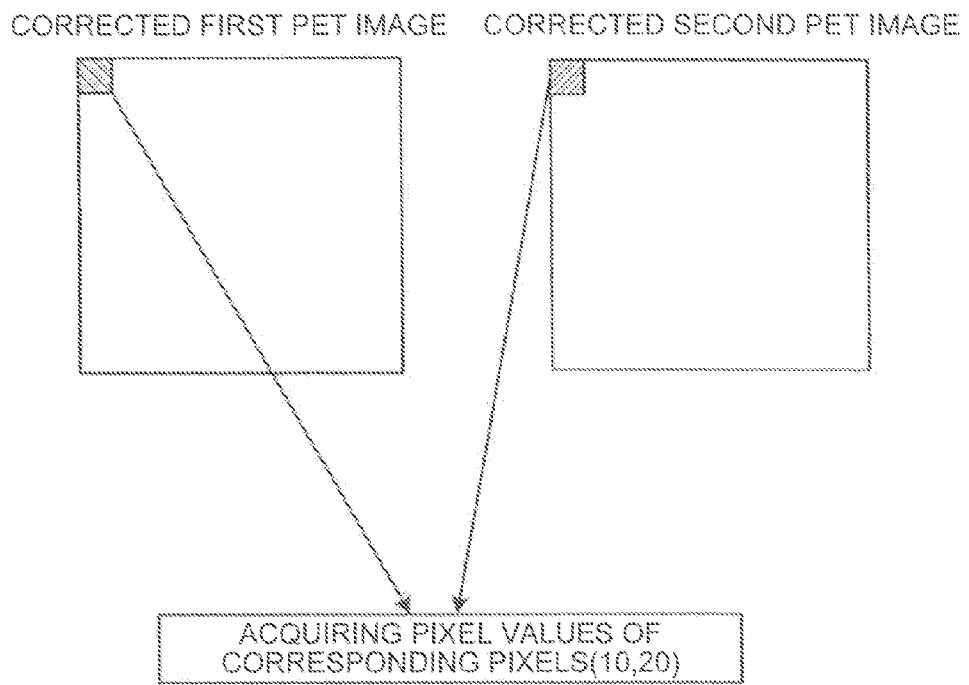
FIGS. 5A and 5B are schematic diagrams for explaining an output-image creating unit.
Figure 5B:
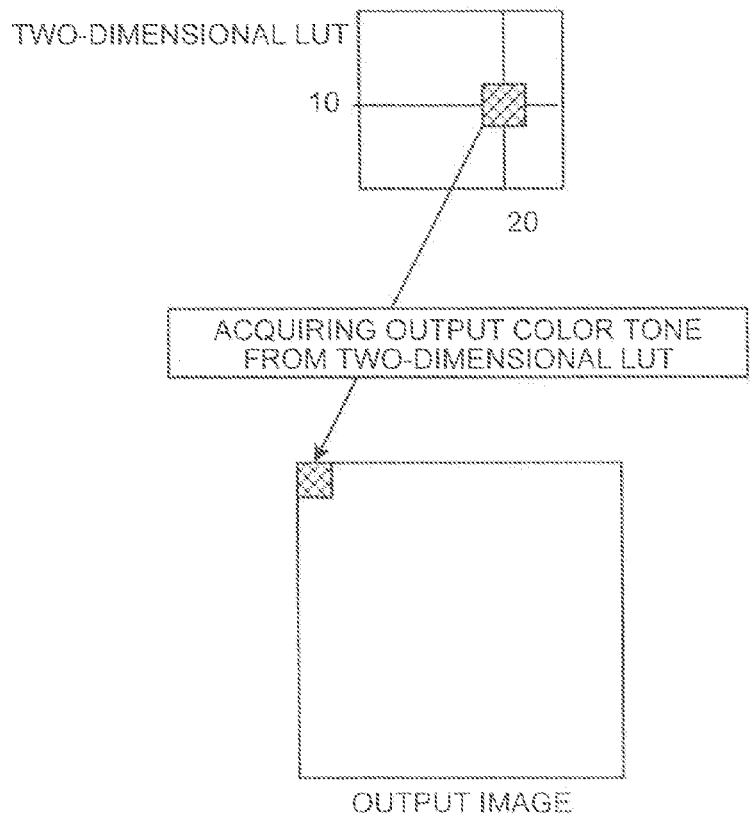
Figure 6A:
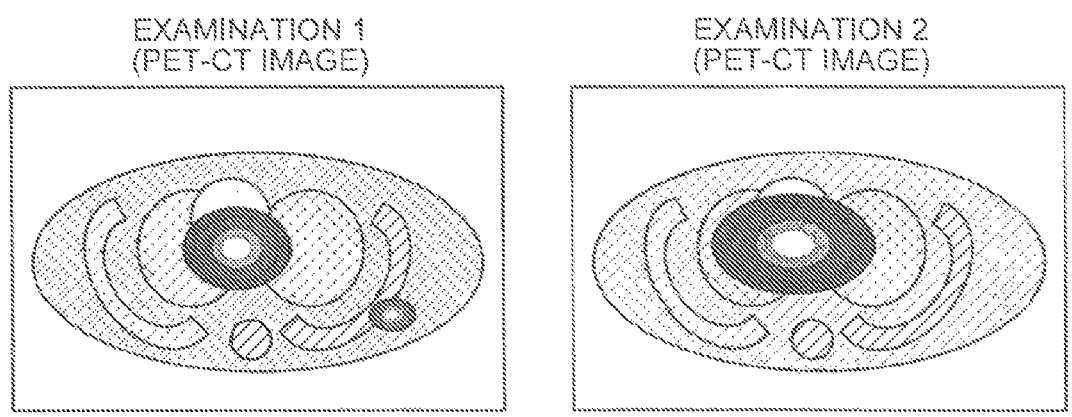
FIGS. 6A and 6B are schematic diagrams for explaining a composite-image creating unit.
Figure 6B:
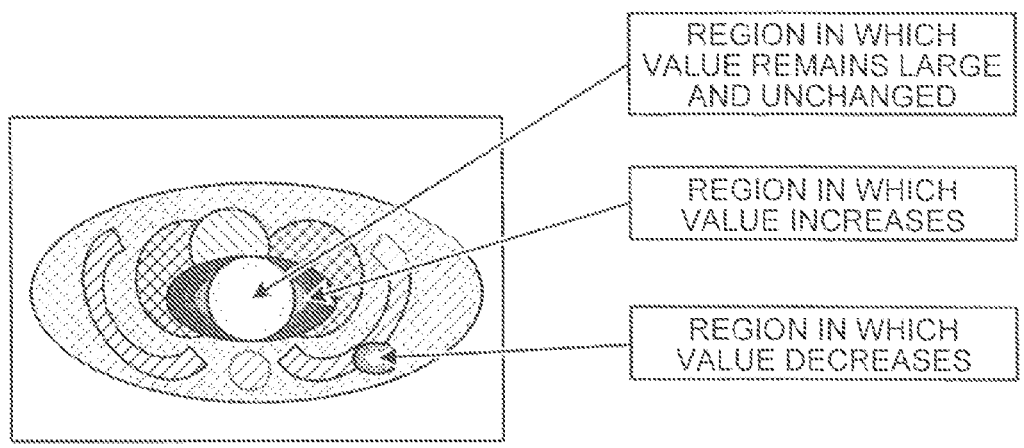

The main feature is explained below with reference to FIGS. 2 to 7B. FIG. 2 is a functional block diagram for explaining a configuration of the data processing apparatus; FIGS. 3A and 3B are schematic diagrams for explaining a registration unit; FIG. 4 is a schematic diagram for explaining a two-dimensional look-up-table (LUT) storage unit; FIGS. 5A and 5B are schematic diagrams for explaining an output-image creating unit; FIGS. 6A and 6B are schematic diagrams for explaining a composite-image creating unit; and FIGS. 7A and 7B, 8A, 8B, and 8C are schematic diagrams for explaining a setting range set on a two-dimensional LUT.

As shown in FIG. 2, the data processing apparatus 4 included in the PET-CT apparatus according to the embodiment includes an image processing unit 41, an image storage unit 42, and a display control unit 43.

The image storage unit 42 stores an image created by the image processing unit 41; and the display control unit 43 reads various images stored by the image storage unit 42, and controls display such that a read image is to be displayed on the monitor of the input-output device 5.

The image processing unit 41 is a device that performs image processing by using projection data created by the PET scanner 1 and the X-ray CT scanner 2, and an image stored by the image storage unit 42; and includes a PET-image creating unit 41a, an X-ray CT-image creating unit 41b, a registration unit 41c, a two-dimensional LUT storage unit 41d, an output-image creating unit 41e, and a composite-image creating unit 41f, as shown in FIG. 2.

The X-ray CT-image creating unit 41b creates as an X-ray CT image an image that is reconstructed by performing back projection on projection data of X-ray collected by the X-ray CT scanner 2, and stores the created X-ray CT image into the image storage unit 42.

The PET-image creating unit 41a creates as a PET image an image that is reconstructed by performing back projection on projection data of gamma-ray collected by the PET scanner 1, and stores the created PET image into the image storage unit 42. The PET-image creating unit 41a can creates a PET image after performing attenuation correction on projection data of gamma-ray, by using the X-ray CT image created by the X-ray CT-image creating unit 41b as an attenuation map.

Image creating processing by the PET-image creating unit 41a and the X-ray CT-image creating unit 41b is to be executed each time when an examination using the PET-CT apparatus is performed. Processing by the registration unit 41c, processing by the output-image creating unit 41e by using the two-dimensional LUT storage unit 41d, and processing by the composite-image creating unit 41f, which are explained below, are then to be performed when a request to start comparative interpretation including designation of PET images to be compared is input via the input-output device 5.

The registration unit 41c performs registration of a first PET image and a second PET image that are PET images created by the PET-image creating unit 41a in two different time period. Specifically, the registration unit 41c executes registration of the first PET image and the second PET image, based on a first CT image and a second CT image with respect to the same portion that are created when the first PET image and the second PET image are created, respectively, by the X-ray CT-image creating unit 41b.

For example, the registration unit 41c reads from the image storage unit 42 the first PET image that is a PET image created during an examination before treatment, and the second PET image that is a PET image created during an examination after treatment, as two PET images that are designated by the doctor. Furthermore, the registration unit 41c reads from the image storage unit 42 the first CT image that is an X-ray CT image created simultaneously when the first PET image is created, and the second CT image that is an X-ray CT image created simultaneously when the second PET image is created.

The registration unit 41c then detects a feature point of tissue morphology rendered on each of the first CT image and the second CT image as shown in FIG. 3A, and calculates a motion vector from respective coordinates of the detected feature points. For example, the registration unit 41c calculates a motion vector of the second CT image with respect to the first CT image.

After that, as shown in FIG. 3B, the registration unit 41c performs registration of the first PET image and the second PET image in accordance with the calculated motion vector, thereby creating a corrected first PET image and a corrected second PET image. For example, the registration unit 41c translates the second PET image by using the motion vector of the second CT image with respect to the first CT image, thereby creating the corrected second PET image on which registration correction has been performed with respect to the first PET image. In such case, the registration unit 41c creates the first PET image itself as a corrected first PET image.

Alternatively, the registration unit 41c can also performs registration through affine transformation using a plurality of motion vectors by detecting a plurality of feature points on two X-ray CT images. In such case, the registration unit 41c performs affine transformation on the first PET image and the second PET image, thereby creating the corrected PET image and the corrected second PET image. The registration unit 41c can also create a corrected first CT image and a corrected second CT image on which registration processing has been performed, by using a motion vector of the second CT image with respect to the first CT image.

Returning to FIG. 2, the two-dimensional LUT storage unit 41d stores a two-dimensional LUT (look up table) in which each of combinations of two input values is associated with an output value for outputting a different color tone. Specifically, the two-dimensional LUT is information that is set with a color-tone pattern obtained by combining a color-tone pattern that light and shade of a color 1 vary in accordance with the level of a first input value, and a color-tone pattern that light and shade of a color 2 different from the color 1 vary in accordance with the level of a second input value.

For example, as shown in FIG. 4, the operator of the PET-CT apparatus sets a color-tone pattern 1 that a gradation pattern of the color 1 is associated with the level of the first input value, and a color-tone pattern 2 that a gradation pattern of the color 2 different from the color 1 is associated with the level of the second input value. As shown in FIG. 4, the operator of the PET-CT apparatus then sets such that an output value corresponding to a color tone composited of a color of the color-tone pattern 1 and a color of the color-tone pattern 2 is to be allocated to each combination of the first input value and the second input value.

Accordingly, the two-dimensional LUT storage unit 41*d* stores a two-dimensional LUT in which different color tones are allocated in accordance with a combination of the first input value and the second input value, as shown in the lower part of FIG. 4. Although color tones to be output are expressed in monotone in the two-dimensional LUT shown in FIG. 4, color tones to be output are expressed in different arbitrary colors in a two-dimensional LUT to be actually stored.

Returning to FIG. 2, the output-image creating unit 41*e* acquires an output value which takes input values from two pixel values of corresponding pixels between the corrected first PET image and the corrected second PET image that are registered by the registration unit 41*c*, from the two-dimensional LUT stored by the two-dimensional LUT storage unit 41*d*; and creates an output image of which pixel values are acquired output values.

Specifically, to begin with, the output-image creating unit 41*e* acquires pixel values (Standard Uptake Value (SUV)) of pixels present on the same coordinates between the corrected first PET image and the corrected second PET image, as the first input value and the second input value. For example, as shown in FIG. 5A, the output-image creating unit 41*e* acquires pixel values "(the first input value, the second input value)=(10, 20)" of respective pixels present on the upper left of the corrected first PET image and the corrected second PET image.

The output-image creating unit 41*e* then acquires an output value corresponding to the combination of (the first input value, the second input value) from the two-dimensional LUT. For example, as shown in FIG. 5B, the output-image creating unit 41*e* acquires an output value (color tone) corresponding to "(the first input value, the second input value)= (10, 20)" from the two-dimensional LUT.

The output-image creating unit 41*e* then creates an output image by taking the output value acquired from the two-dimensional LUT for a pixel value of the pixel at the position at which (the first input value, the second input value) is acquired, as shown in FIG. 5B. The output-image creating unit 41*e* stores the created output image into the image storage unit 42.

Returning to FIG. 2, when a request to display a composite image is received via the input-output device 5 from the doctor who performs comparative interpretation, the composite-image creating unit 41*f* creates a composite image that is composited of an output image created by the output-image creating unit 41*e* and an X-ray CT image. For example, the composite-image creating unit 41*f* creates a composite image that is composited of an output image and the corrected second PET image created by the registration unit 41*c*. The composite-image creating unit 41*f* can also create a PET-CT image that is composited of a PET image and an X-ray CT image both of which are created through the same examination.

For example, according to respective PET-CT images of the examination 1 before treatment and the examination 2 after treatment, as shown in FIG. 6A, a tumor region in which a labeled compound is taken up and accumulated is rendered in tones of a single color (for example, a gradation of black and white), together with morphological information.

According to a composite image of an output image created by the image processing unit 41 according to the embodiment and an X-ray CT image, as shown in FIG. 6B, a region in which an SUV value remains large and unchanged between the examination 1 and the examination 2 (a region where there is no treatment effect), a region in which an SUV value increases (a region where metastasis of cancer occurs after treatment), and a region in which an SUV value decreases (a region where there is a treatment effect) are rendered in respective different color tones. Moreover, according to the output image shown in FIG. 6B, changes in the tumor region between the examination 1 and the examination 2 are rendered in color tones to which levels of SUV values of the original PET images are reflected.

Returning to FIG. 2, when a request to display an output image is received via the input-output device 5 from the doctor who performs comparative interpretation, the display control unit 43 reads an output image created by the output-image creating unit 41*e* from the image storage unit 42, and controls display such that the output image is to be displayed on the monitor of the input-output device 5.

Moreover, when a request to display a composite image is received via the input-output device 5 from the doctor who performs comparative interpretation, the display control unit 43 reads a composite image created by the composite-image creating unit 41*f* from the image storage unit 42, and controls display such that the composite image is to be displayed on the monitor of the input-output device 5. For example, when a request to display a composite image is received via the input-output device 5 from the doctor who performs comparative interpretation, the display control unit 43 causes the monitor to display a composite image as shown in FIG. 6B.

Although explained above is a case where an output image is created by using all output values corresponding to first input values and second input values acquired by the output-image creating unit 41*e* from the two-dimensional LUT; the embodiment is not limited to this, and can be applied to a case where only when an output value corresponding to a first input value and a second input value acquired by the output-image creating unit 41*e* from the two-dimensional LUT falls within a setting range preliminarily specified by the operator on the two-dimensional LUT, the output value is taken for the pixel value of a pixel to be included in an output image, whereby the output image is created.

A setting range on a two-dimensional LUT set by an operator (such as a doctor) according to the embodiment is explained below with reference to FIGS. 7A, 7B, 8A, 8B, and 8C.

Specifically, when a request to set a setting range is received via the input-output device 5 from the doctor who performs comparative interpretation, the display control unit 43 causes the monitor to display the two-dimensional LUT stored by the two-dimensional LUT storage unit 41*d* (see the lower figure of FIG. 4). The doctor then sets a setting range based on information to which the doctor intends to refer on an output image, by using, for example, a mouse that the input-output device 5 includes. Specifically, a setting range is set for rendering on an output image a region in which pixel values of pixels of the corrected first PET image or the corrected second PET image are larger than a certain value.

Figure 7A:
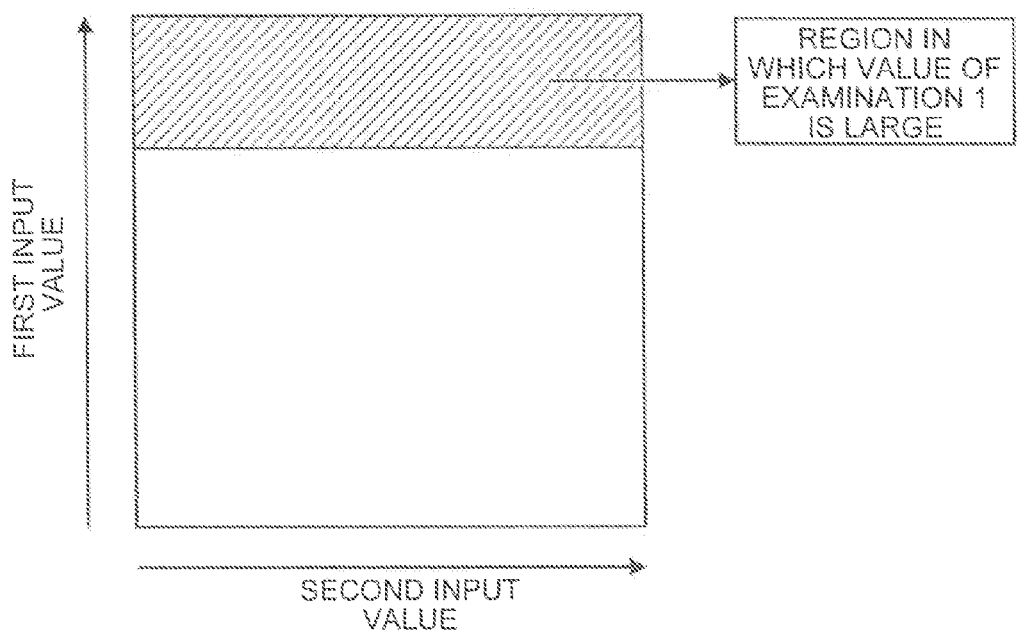
FIGS. 7A and 7B, 8A, 8B, and 8C are schematic diagrams for explaining a setting range set on a two-dimensional LUT.

For example, when the doctor who performs comparative interpretation specifies a setting range as shown in FIG. 7A, only "a region in which values of the examination 1 are larger than a certain value" is to be rendered together with information about values of the examination 2 on an output image created by the output-image creating unit 41e. In other words, the doctor can grasp whether a treatment is effective on each tumor region in which a labeled compound is substantially accumulated before treatment, by referring to the output image.

Figure 7B:
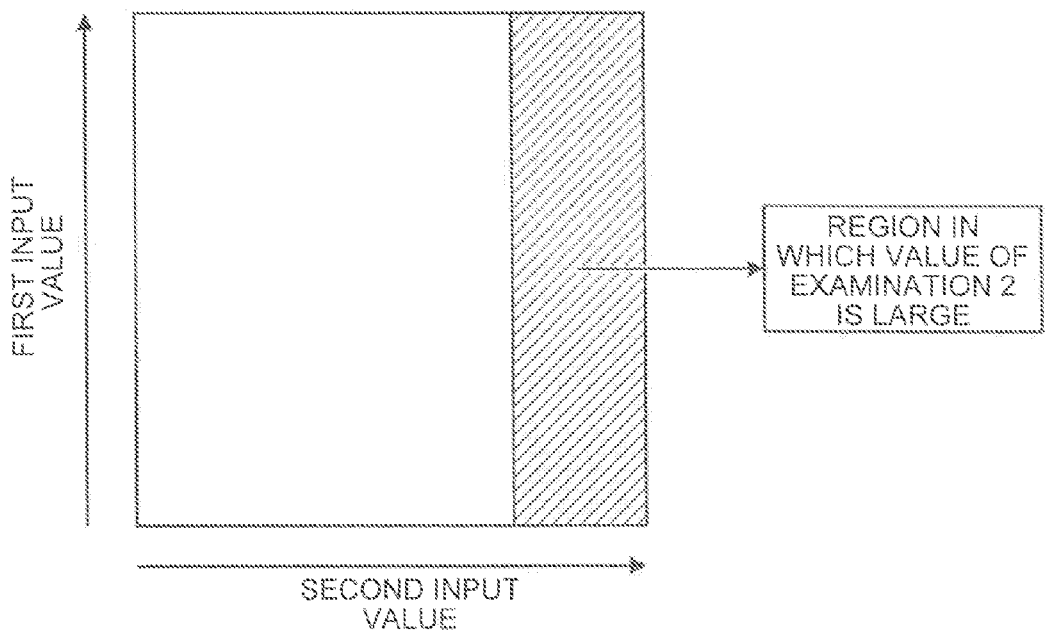

Moreover, when the doctor who performs comparative interpretation specifies a setting range as shown in FIG. 7B, only "a region in which values of the examination 2 are larger than a certain value" is to be rendered together with information about values of the examination 1 on an output image created by the output-image creating unit 41e. In other words, the doctor can grasp a state before treatment of each tumor region in which a labeled compound is still substantially accumulated even after treatment, by referring to the output image.

Furthermore, a setting range can be set to render on an output image a region in which the pixel value of corresponding pixels between the corrected first PET image and the corrected second PET image increases between the images, and/or a region in which the pixel value decreases between the images.

Figure 8A:
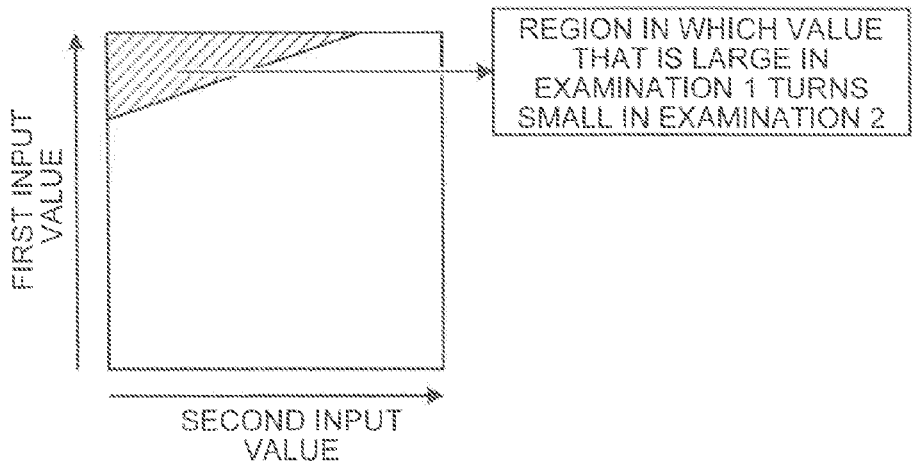

For example, when the doctor who performs comparative interpretation specifies a setting range as shown in FIG. 8A, "a region in which a value that is large in the examination 1 turns small in the examination 2" is to be rendered together with information about respective original values of the examination 1 and the examination 2 on an output image created by the output-image creating unit 41e. In other words, the doctor can grasp a region in which it is determined that there is a treatment effect, because of decrease in accumulation of a labeled compound, by referring to the output image.

Figure 8B:
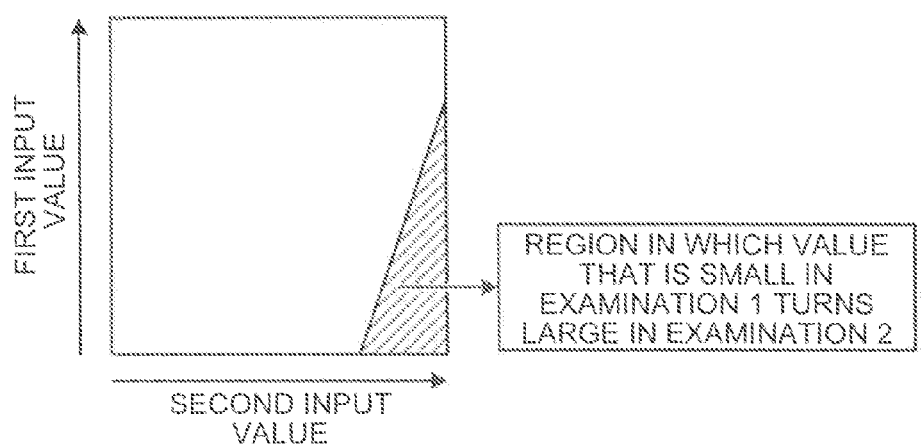

Moreover, when the doctor who performs comparative interpretation specifies a setting range as shown in FIG. 8B, "a region in which a value that is small in the examination 1 turns large in the examination 2" is to be rendered together with information about respective original values of the examination 1 and the examination 2 on an output image created by the output-image creating unit 41e. In other words, the doctor can grasp a region in which it is determined that there is no treatment effect, or a region into which a tumor has metastasized, because of increase in accumulation of a labeled compound, by referring to the output image.

Figure 8C:
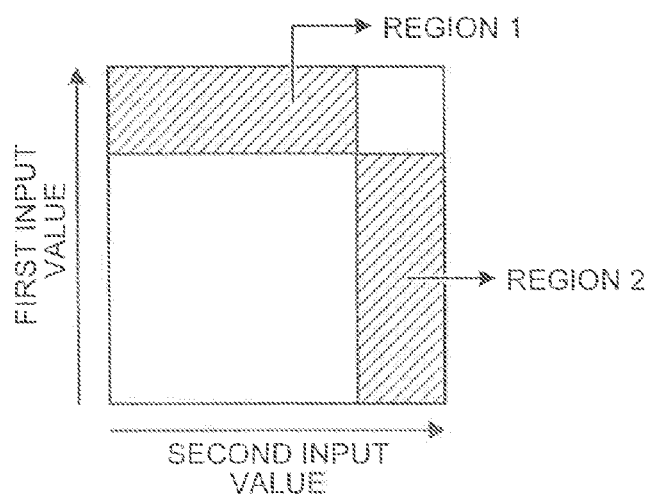

Furthermore, when the doctor who performs comparative interpretation specifies a setting range as shown in FIG. 8C, "'a region 1" in which values are equal to or higher than a value 1 in the examination 1 and turn equal to or lower than a value 2 in the examination 2', and "a region 2" in which values are equal to or lower than the value 1 in the examination 1 and turn equal to or higher than the value 2 in the examination 2" are to be rendered on an output image created by the output-image creating unit 41e, together with information about respective original values of the examination 1 and the examination 2. In other words, the doctor can grasp a region in which a labeled compound is accumulated equal to or more than a certain value (the value 1) and then turns equal to or less than a certain value (the value 2) because of a treatment effect, and a region in which a labeled compound is accumulated equal to or less than the certain value (the value 1) and then turns equal to or more than the certain value (the value 2) due to, for example, metastasis after treatment, by simultaneously distinguishing them from each other.

The doctor can cause an output image to be displayed by individually setting the region 1 and the region 2. Moreover, the doctor can cause an output image to be displayed by simultaneously specifying setting ranges shown in FIGS. 7A and 7B, and setting ranges shown in FIGS. 8A and 8B. The output-image creating unit 41e creates an output image by allocating an output value by which a color tone to be displayed is "white" or "black" to a pixel of which acquired output value does not fall in the setting range.

Examination-result display processing by the PET-CT apparatus according to the embodiment is explained below with reference to FIG. 9. FIG. 9 is a flowchart for explaining examination-result display processing by the PET-CT apparatus according to the embodiment. The following description explains processing to be executed after a PET image and an X-ray CT image of the examination 2 subjected to comparative interpretation with respect to the examination 1 are created by the PET-image creating unit 41a and the X-ray CT-image creating unit 41b, respectively.

As shown in FIG. 9, when the PET-CT apparatus according to the embodiment receives a request to start comparative interpretation including designation of PET images to be compared from the doctor via the input-output device 5 (Yes at Step S101); the PET-CT apparatus according to the embodiment reads two pairs of images subjected to interpretation from the image storage unit 42, namely, the PET images of the examination 1 and the examination 2 specified by the doctor, and X-ray CT images that are created simultaneously with the PET images in the examination 1 and the examination 2 (Step S102).

The registration unit 41c then registers the PET images of the examination 1 and the examination 2 by using the X-ray CT images of the examination 1 and the examination 2 (Step S103). Specifically, the registration unit 41c calculates a vector motion from the first CT image (an X-ray CT image of the examination 1) and the second CT image (an X-ray CT image of the examination 2) of the same portion that are created when the first PET image (a PET image of the examination 1) and the second PET image (a PET image of the examination 2) are created, respectively, by the X-ray CT-image creating unit 41b. The registration unit 41c then executes registration of the first PET image and the second PET image by using the calculated motion vector.

After that, the output-image creating unit 41e determines whether a setting range is received from the doctor who refers to the two-dimensional LUT (Step S104).

If setting range is not received on the two-dimensional LUT (No at Step S104); the output-image creating unit 41e acquires output values each of which takes input values from a combination of pixel values of corresponding pixels on the two registered PET images, from the two-dimensional LUT stored by the two-dimensional LUT storage unit 41d, and creates an output image (Step S105).

By contrast, if a setting range is received on the two-dimensional LUT (Yes at Step S104); the output-image creating unit 41e acquires output values each of which takes input values from a combination of pixel values of corresponding pixels on the two registered PET images, from the two-dimensional LUT stored by the two-dimensional LUT storage unit 41d (Step S106); and creates an output image only from output values within the setting range among the acquired output values (Step S107).

The composite-image creating unit 41f then determines whether a request for composite display with an X-ray CT image is received from the doctor (Step S108).

If request for composite display with an X-ray CT image is not received (No at Step S108); in accordance with a notice from the composite-image creating unit 41f, the display control unit 43 controls display such that the output image created by the output-image creating unit 41e at Step S105 or Step S107 and stored by the image storage unit 42 is to be displayed on the monitor of the input-output device 5 (Step S111); and then the processing is terminated.

By contrast, if a request for composite display of an X-ray CT image is received (Yes at Step S108); the composite-image creating unit 41f combines an X-ray CT image and the output image created by the output-image creating unit 41e at Step S105 or Step S107 and stored by the image storage unit 42, and creates a composite image (Step S109). For example, the composite-image creating unit 41f combines the output image and the X-ray CT image that is created in the examination 2, and registered by the registration unit 41c.

The display control unit 43 then controls display such that the composite image created by the composite-image creating unit 41f and stored by the image storage unit 42 is to be displayed on the monitor of the input-output device 5 (Step S110), and the processing is terminated.

As described above, according to the embodiment, the two-dimensional LUT storage unit 41d stores a two-dimensional LUT in which each of combinations of two input values is associated with an output value for outputting a different color tone. The registration unit 41c then registers PET images of the examination 1 and the examination 2 by using X-ray CT images of the examination 1 and the examination 2 subjected to comparative interpretation; and the output-image creating unit 41e acquires output values each of which takes input values from a combination of pixel values of corresponding pixels on the two registered PET images, from the two-dimensional LUT, and creates an output image. When a setting range is specified on the two-dimensional LUT, the output-image creating unit 41e acquires output values each of which takes input values from a combination of pixel values of corresponding pixels on the two registered PET images, from the two-dimensional LUT, and creates an output image only from output values within the setting range among the acquired output values.

The display control unit 43 then controls display such that an output image, or a composite image of an output image and an X-ray CT image created by the composite-image creating unit 41f is to be displayed on the monitor of the input-output device 5. On the output image, change in the degree of accumulation of a labeled compound among PET images created in different time periods is rendered in a state including information about SUV values of original PET images. For example, according to a conventional differential image, any location where an SUV value decreases by "five" between the examination 1 and the examination 2 is expressed in the same color tone; however, on an output image displayed according to the embodiment, for example, a location where an SUV value decreases from "100" to "95" between the examination 1 and the examination 2 and a location where an SUV value decreases from "10" to "5" between the examination 1 and the examination 2 can be expressed in different color tones. Therefore, according to the embodiment, as described above as the main feature, image diagnosis by a doctor who compares a plurality of examination results by using PET images can be surely assisted by displaying an output image. Moreover, instead of performing image diagnosis by displaying PET images in parallel layout, image diagnosis can be performed only by referring to one output image, so that diagnosis efficiency by a doctor when performing image diagnoses for a plurality of patients can be improved.

Furthermore, according to the embodiment, a two-dimensional LUT is stored into the two-dimensional LUT storage unit 41d as information that is set with a color-tone pattern obtained by combining a color-tone pattern that light and shade of the color 1 vary in accordance with the level of the first input value, and a color-tone pattern that light and shade of a color 2 different from the color 1 vary in accordance with the level of the second input value.

Therefore, according to the embodiment, by taking a warm color for the color 1 and taking a cold color for the color 2, the color tone of an output value can be surely changed with respect to each of combinations of two SUV values.

Moreover, according to the embodiment, by specifying a setting range, only a region representing a characteristic change to which a doctor desires to refer can be displayed together with information about original values of examination results, so that image diagnosis by a doctor who compares a plurality of examination results by using PET images can be surely assisted.

Furthermore, according to the embodiment, an X-ray CT image on which morphological information is rendered can be displayed over an output image in a superimposed manner, so that image diagnosis by a doctor who compares a plurality of examination results by using PET images can be surely assisted.

The embodiment is explained above in a case where each of the examinations for performing comparative interpretation is carried out before and after treatment. However, the embodiment can be applied to any case as long as where two examinations performed at different arbitrary time points are compared, for example, two times of examinations to be performed for followup after treatment.

Moreover, although the embodiment is explained above in a case of acquiring an output value from a two-dimensional LUT by taking the pixel value of a pixel of a PET image of the examination 1 for the first input value, and taking the pixel value of a pixel of a PET image of the examination 2 for the second input value; the embodiment is not limited to this, and can be applied to a case of acquiring an output value from a two-dimensional LUT by taking the pixel value of a pixel of a PET image of the examination 2 for the first input value, and taking the pixel value of a pixel of a PET image of the examination 1 for the second input value.

Furthermore, although the embodiment is explained above in a case of using a PET apparatus as a nuclear medical imaging apparatus, the embodiment can be applied to a case of using a SPECT apparatus or a gamma camera as a nuclear medical imaging apparatus.

Moreover, the embodiment is explained above in a case of a nuclear medical imaging apparatus that is integrated with an X-ray CT apparatus. However, the embodiment can also be applied to a nuclear medical imaging apparatus that is provided separately from an X-ray CT apparatus, as long as an X-ray CT image of the same portion as the position of a nuclear medical image can be created.

Furthermore, although the embodiment is explained above in a case of acquiring tissue morphological information about an examination portion of the subject P by using an X-ray CT apparatus; the embodiment can be applied to a case of acquiring a Magnetic Resonance Imaging (MRI) image created by an MRI apparatus as tissue morphological information about an examination portion of the subject P. In other words, the embodiment can be applied to a case where registration of nuclear medical images is performed with respect to MRI images created in respective examinations, and an MRI image is to be combined with an output image.

Moreover, the embodiment is explained above in a case where creation and display of an output image and creation and display of a composite image are performed by a nuclear medical imaging apparatus, such as a PET apparatus, a SPECT apparatus, a PET-CT apparatus, or a SPECT-CT apparatus. However, the embodiment can be applied to a case where the creation and the display of an output image and the creation and the display of a composite image explained in the above embodiment are performed by an image processing apparatus that is provided separately from a nuclear medical imaging apparatus. By using such image processing apparatus, when an output image and/or a composite image are created from nuclear medical images and tissue images and displayed, image diagnosis by a doctor who compares a plurality of examination results by using nuclear medical images can be surely assisted.

Furthermore, the embodiment is explained above in a case where a plurality of examination results is compared by using nuclear medical images. However, the embodiment can be applied to a case where a plurality of examination results is compared by using other medical images, for example, X-ray images, X-ray CT images, MRI images, and ultrasound images. A perfusion image created by, for example, an X-ray CT apparatus or an MRI apparatus, can be listed as such medical image. In addition, a medical image onto which a calcified portion is imaged by an X-ray diagnosis apparatus, an X-ray CT apparatus, or an ultrasound diagnosis apparatus, or a functional Magnetic Resonance Imaging (fMRI) image created by an MRI apparatus can be listed as such medical image.

When such medical images are created in two different time periods, similarly to comparative interpretation of nuclear medical images, the doctor cannot grasp information about respective original values of the medical images to be compared, by referring to a differential image. For this reason, the image processing apparatus described above performs registration between a first medical image and a second medical image. The image processing apparatus then acquires output values each of which takes input values from a combination of pixel values of corresponding pixels between the two registered medical images, from a two-dimensional LUT, and creates an output image. Moreover, when a setting range is specified on the two-dimensional LUT, the image processing apparatus acquires output values each of which takes input values from a combination of pixel values of corresponding pixels between the two registered medical images, from a two-dimensional LUT; and creates an output image from only output values within the setting range among the acquired output values. The image processing apparatus then displays the output image. Such output image is an image that reflects information about respective original values of the medical images to be compared.

Accordingly, the doctor can grasp states of a blood flow before and after a treatment for a brain ischemia, states of a calcified portion before and after a treatment for a breast cancer, or states of recovery of a language area before and after a treatment for a speech impediment, by referring to the output image. In other words, the embodiments can ensure assistance in image diagnosis by a doctor, even when comparing a plurality of examination results by using medical images other than nuclear medical images.

While certain embodiments have been described, these embodiments have been presented by way of example only, and are not intended to limit the scope of the invention. Indeed, the novel apparatuses and methods described herein may be embodied in a variety of other forms; furthermore, various omissions, substitutions and changes in form of the apparatuses and methods described herein may be made without departing from the spirit of the invention. The accompanying claims and their equivalents are intended to cover such forms or modifications as would fall within the scope and spirit of the invention.

What is claimed is:

1. A nuclear medical imaging apparatus, comprising:
a nuclear medical scanner configured to obtain projection data by detecting radiation emitted by a nuclide given to a subject;
a processing circuit configured to create first and second nuclear medical images of a portion of the subject from the obtained projection data; and
a memory to store two-dimensional association information in which each of combinations of two first values is associated with a second value for outputting an associated color tone, wherein the associated color tone for a first combination is different from the associated color tone for a second combination even though a difference value between the two first values of said first combination is identical to a difference value between the two first values of the second combination, wherein the processing circuit is further configured to
execute registration of the first nuclear medical image and the second nuclear medical image, the first and second nuclear medical images being created in two different time periods, the registration being based on a first tissue image of the portion of the subject acquired at a time of acquisition of the first nuclear medical image and a second tissue image of the portion of the subject acquired at a time of acquisition of the second nuclear medical image,
acquire a plurality of output values, each output value being determined from a pair of input values that are two pixel values of corresponding pixels of the first nuclear medical image and the second nuclear medical image that are registered by the processing circuit, from the two-dimensional association information stored by the memory, and to create an output nuclear medical image having pixel values that are the acquired output values, and
control a display to display the output nuclear medical image.

2. The nuclear medical imaging apparatus according to claim 1, wherein the two-dimensional association information is information that is set in accordance with a color-tone pattern obtained by combining a color-tone pattern in which light and shade of a first color vary in accordance with a level of a first input value, and a color-tone pattern in which light and shade of a second color different from the first color vary in accordance with a level of a second input value.

3. The nuclear medical imaging apparatus according to claim 1, wherein the processing circuit is further configured to acquire each output value, and only when the acquired output value falls within a setting range set to restrict output values in the two-dimensional association information used for creating the output nuclear medical image, the acquired output value is taken for a pixel value of a pixel included in the output nuclear medical image.

4. The nuclear medical imaging apparatus according to claim 3, wherein the setting range is a range that is set for rendering on the output nuclear medical image a region in which one of a pixel value of a pixel of the first nuclear medical image that is registered and a pixel value of a pixel of the second nuclear medical image that is registered becomes larger than a predetermined value.

5. The nuclear medical imaging apparatus according to claim 3, wherein the setting range is a range that is set for rendering on the output nuclear medical image at least one of a region in which a pixel value of corresponding pixels between the first nuclear medical image and the second nuclear medical image that are registered increases between the first and second nuclear medical images, and/or a region in which the pixel value decreases between the first and second nuclear medical images.

6. The nuclear medical imaging apparatus according to claim 1, wherein the processing circuit is further configured to create a composite image of the output nuclear medical image and the second tissue image, and to control the display to display the composite image.

7. The nuclear medical imaging apparatus according to claim 1, wherein the first tissue image is an X-ray CT image with respect to the portion of the subject and is created by an X-ray CT apparatus.

8. An image processing apparatus, comprising:
a memory configured to store two-dimensional association information in which each of combinations of two first values is associated with a second value for outputting an associated color tone, wherein the associated color tone for a first combination is different from the associated color tone for a second combination even though a difference value between the two first values of said first combination is identical to a difference value between the two first values of the second combination; and
a processing circuit configured to
execute registration of a first image and a second image, the first and second images being medical images created by a medical image diagnostic apparatus in two different respective time periods;
acquire a plurality of output values, each output value being determined from a pair of input values that are two pixel values of corresponding pixels of the first image and the second image that are registered by the processing circuit, from the two-dimensional association information stored by the memory, and to create an output medical image having pixel values that are the acquired output values; and
control a display to display the output medical image.

9. An image processing method, comprising:
obtaining, by a nuclear medical scanner, projection data by detecting radiation emitted by a nuclide given to a subject;
creating first and second nuclear medical images of a portion of the subject from the obtained projection data;
storing, by a memory, two-dimensional association information in which each of combinations of two first values is associated with a second value for outputting an associated color tone, wherein the associated color tone for a first combination is different from the associated color tone for a second combination even though a difference value between the two first values of said first combination is identical to a difference value between the two first values of the second combination;
executing, by a processing circuit connected to the memory, registration of the first nuclear medical image and the second nuclear medical image, the first and second nuclear medical images being created in two different time periods, the registration being based on a first tissue image of the portion of the subject acquired at a time of acquisition of the first nuclear medical image and a second tissue image of the portion of the subject acquired at a time of acquisition of the second nuclear medical image;
acquiring a plurality of output values, each output value being determined from a pair of input values that are two pixel values of corresponding pixels of the first nuclear medical image and the second nuclear medical image that are registered by the processing circuit, from the two-dimensional association information stored by the memory, and creating an output nuclear medical image having pixel values that are the acquired output values; and
controlling a display to display the output nuclear medical image.

10. The image processing method according to claim 9, wherein the two-dimensional association information is information that is set in accordance with a color-tone pattern obtained by combining a color-tone pattern in which light and shade of a first color vary in accordance with a level of a first input value, and a color-tone pattern in which light and shade of a second color different from the first color vary in accordance with a level of a second input value.

11. The image processing method according to claim 9, wherein the processing circuit is configured to acquire each output value, and only when the acquired output value falls within a setting range set to restrict output values in the two-dimensional association information used for creating the output nuclear medical image, the acquired output value is taken for a pixel value of a pixel included in the output nuclear medical image.

12. The image processing method according to claim 11, wherein the setting range is a range that is set for rendering on the output nuclear medical image a region in which one of a pixel value of a pixel of the first nuclear medical image that is registered and a pixel value of a pixel of the second nuclear medical image that is registered becomes larger than a predetermined value.

13. The image processing method according to claim 11, wherein the setting range is a range that is set for rendering on the output nuclear medical image at least one of a region in which a pixel value of corresponding pixels between the first nuclear medical image and the second nuclear medical image that are registered increases between the first and second nuclear medical images, and a region in which the pixel value decreases between the first and second nuclear medical images.

14. The image processing method according to claim 9, wherein the processing circuit is further configured to create a composite image of the output nuclear medical image and the second tissue image, and to control the display to display the composite image.

15. The image processing method according to claim 9, wherein the first tissue image is an X-ray CT image with respect to the portion of the subject and is created by an X-ray CT apparatus.

16. An image processing method, comprising:
storing, by a memory, two-dimensional association information in which each of combinations of two first values is associated with a second value for outputting an associated color tone, wherein the associated color tone for a first combination is different from the associated color tone for a second combination even though a difference value between the two first values of said first combination is identical to a difference value between the two first values of the second combination;
executing, by a processing circuit connected to the memory, registration between a first image and a second image, the first and second images being medical images created by a medical image diagnostic apparatus in two different respective time periods;

acquiring a plurality of output values, each output value being determined from a pair of input values that are two pixel values of corresponding pixels of the first image and the second image that are registered, from the two-dimensional association information stored by the memory, and creating an output medical image having pixel values that are the acquired output values; and
controlling a display to display the output medical image.

* * * * *